(12) United States Patent
Lugo

(10) Patent No.: US 6,287,252 B1
(45) Date of Patent: Sep. 11, 2001

(54) PATIENT MONITOR

(75) Inventor: Michael V. Lugo, Lake Forrest, CA (US)

(73) Assignee: Monitrak, Irvine, CA (US)

( * ) Notice: Subject to any disclaimer, the term of this patent is extended or adjusted under 35 U.S.C. 154(b) by 0 days.

(21) Appl. No.: 09/343,320

(22) Filed: Jun. 30, 1999

(51) Int. Cl.$^7$ ........................................ A61B 5/00
(52) U.S. Cl. ............................... 600/300; 128/903
(58) Field of Search .................... 600/300, 301, 600/481, 508, 545, 529; 128/903, 904

(56) References Cited

U.S. PATENT DOCUMENTS

| | | | |
|---|---|---|---|
| D. 392,043 | 3/1998 | Cooper et al. ................ D24/186 |
| 3,841,315 | * 10/1974 | Kopp ................................ 600/519 |
| 4,187,854 | * 2/1980 | Hepp et al. ...................... 607/33 |
| 4,195,642 | * 4/1980 | Price et al. ...................... 600/502 |
| 4,494,552 | * 1/1985 | Heath .............................. 600/509 |
| 4,537,200 | * 8/1985 | Widrow ........................... 600/509 |
| 4,592,018 | * 5/1986 | Wiegman ........................ 365/63 |
| 4,803,997 | * 2/1989 | Bowman ......................... 600/536 |
| 5,012,229 | * 4/1991 | Lennon et al. ................... 345/1 |
| 5,022,404 | * 6/1991 | Hafner ............................ 600/508 |
| 5,027,824 | * 7/1991 | Dougherty et al. ............. 600/519 |
| 5,153,584 | * 10/1992 | Engira ............................. 128/903 |
| 5,331,549 | * 7/1994 | Crawford, Jr. .................. 600/513 |
| 5,335,666 | * 8/1994 | Bowman et al. ................ 600/536 |
| 5,336,245 | * 8/1994 | Adams Theodore P. et al. .. 128/904 |
| 5,400,794 | * 3/1995 | Gorman ........................... 600/508 |
| 5,432,698 | * 7/1995 | Fujita ............................... 600/301 |
| 5,449,345 | * 9/1995 | Taylor et al. .................... 604/100.03 |
| 5,462,051 | * 10/1995 | Oka et al. ........................ 128/903 |
| 5,473,536 | * 12/1995 | Wimmer ......................... 700/90 |
| 5,529,073 | * 6/1996 | Kielbasiewicz ................. 600/509 |
| 5,537,459 | * 7/1996 | Price ................................ 455/435 |
| 5,544,649 | * 8/1996 | David et al. ..................... 128/904 |
| 5,544,661 | * 8/1996 | Davis et al. ..................... 128/904 |
| 5,558,096 | * 9/1996 | Palatnik ........................... 600/500 |
| 5,560,352 | * 10/1996 | Heim ............................... 128/203.12 |
| 5,590,650 | * 1/1997 | Genova ............................ 600/301 |
| 5,623,925 | * 4/1997 | Swenson ......................... 600/301 |
| 5,671,734 | * 9/1997 | Pugh ................................ 600/301 |
| 5,678,568 | * 10/1997 | Uchikubo ........................ 128/897 |
| 5,687,734 | * 11/1997 | Dempsey ........................ 600/509 |
| 5,729,203 | * 3/1998 | Oka et al. ........................ 128/903 |
| 5,742,233 | * 4/1998 | Hoffman et al. ................ 340/573.1 |
| 5,792,068 | * 8/1998 | Bowman et al. ................ 600/536 |
| 5,832,448 | 11/1998 | Brown ............................. 705/2 |
| 5,855,550 | 1/1999 | Lai et al. ......................... 600/300 |
| 5,942,986 | 8/1999 | Shabot et al. ................... 340/825.44 |
| 5,944,659 | * 8/1999 | Flach et al. ..................... 600/300 |
| 5,954,793 | 9/1999 | Stutman et al. ................. 709/204 |
| 5,966,692 | 10/1999 | Langer et al. ................... 705/3 |
| 5,974,389 | 10/1999 | Clark et al. ..................... 705/3 |
| 5,984,502 | 11/1999 | Calder ............................. 700/83 |
| 6,001,057 | 12/1999 | Bongiovanni et al. ......... 600/21 |
| 6,004,276 | 12/1999 | Wright et al. ................... 600/508 |
| 6,014,346 | 1/2000 | Malone ........................... 368/10 |
| 6,039,688 | 3/2000 | Douglas et al. ................. 600/300 |
| 6,050,940 | 4/2000 | Braun et al. .................... 600/300 |
| 6,076,016 | * 6/2000 | Feierbach ........................ 128/903 |
| 6,083,248 | * 7/2000 | Thompson ...................... 607/30 |
| 6,113,539 | * 9/2000 | Ridenour ........................ 600/300 |

* cited by examiner

*Primary Examiner*—John P. Lacyk
*Assistant Examiner*—Charles Marmor, II
(74) *Attorney, Agent, or Firm*—Fish & Richardson P.C.

(57) ABSTRACT

An apparatus for monitoring physiological data generated by sensors disposed on or in a patient. The apparatus includes an interface operable to receive data signals generated by the sensors and a data processor coupled to the interface and operable to format data signals received from the interface into one or more frames of data where each frame includes a transmitter identifier that is unique to the apparatus. A transmitter is included that is operable to receive the frames from the data processor and broadcast the frames using radio frequency signals to a local receiver located in close proximity to the patient. A patch is adhesively attached to the patient and has a first surface on which the interface, data processor and transmitter are disposed.

23 Claims, 8 Drawing Sheets

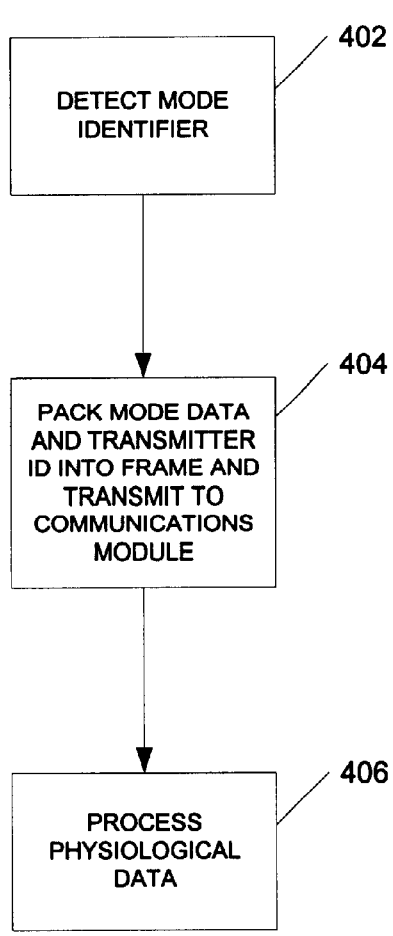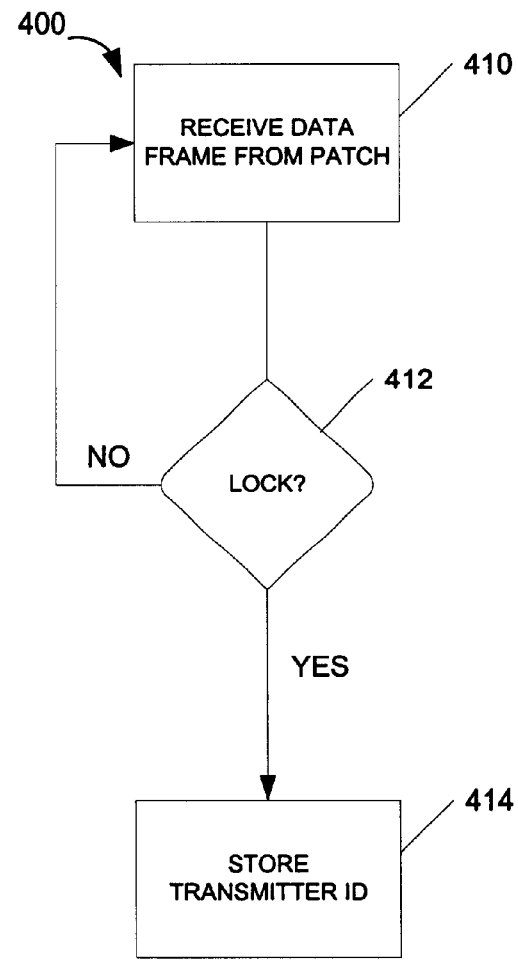
Figure 4a
Figure 4b

PATIENT MONITOR

BACKGROUND

The present invention relates generally to medical devices, and more particularly to methods and apparatus for remotely monitoring physiological signals for a patient.

Managed health care providers are redefining the practice of medicine in this country. Managed health care providers continually search for means to cut costs while maintaining patient services. One example of cost consciousness is found in the growth of outpatient surgery services presently offered. Certain surgery services are being offered today on an outpatient basis that would have ordinarily resulted in a two or three day hospital stay just a few years ago. Since the services are classified as outpatient, the providers save money on hospital expenses.

For various reasons including advances in the medical arts and the prevalence of managed care, a growing trend has emerged to accelerate the discharge of patients from a hospital when the services provided are on an inpatient basis. As such, care givers and managed health care providers alike are increasingly looking for methods which facilitate the early release of patients with out jeopardizing patient care.

Certain health care events require monitoring of one or more patient physiological signals. For example, patients vital signs are monitored in a recovery room after inpatient surgery procedures. Typically, vital signs for a plurality of patients are maintained by a central station, with each patient separately "wired" into the system. While these systems are beneficial to monitor the patient's recovery, the systems are costly and are not readily portable.

When a patient is "out of danger", he or she can be moved back to a room or ward. There, once again, various vital signs of the patient may be monitored by a second central system responsible for maintaining information for each patient in a room, a ward or other grouping of patients. These second type monitoring systems typically do not monitor as many physiological signals, since in most cases the patient is perceived to be out of significant danger. While this may reduce some costs, again this type of monitoring system is typically costly and not readily portable.

SUMMARY OF THE INVENTION

In general, in one aspect, the invention provides an apparatus for monitoring physiological data generated by sensors disposed on or in a patient. The apparatus includes an interface operable to receive data signals generated by the sensors and a data processor coupled to the interface and operable to format data signals received from the interface into one or more frames of data where each frame includes a transmitter identifier that is unique to the apparatus. A transmitter is included that is operable to receive the frames from the data processor and broadcast the frames using radio frequency signals to a local receiver located in close proximity to the patient. A patch is attached to the patient and has a first surface on which the interface, data processor and transmitter are disposed.

Aspects of the invention can include one or more of the following features. The patch can be attached using an adhesive. The interface can include a connector and a power interlock. The connector couples lead wires from the sensors to the apparatus. The power interlock is operable to disable the apparatus when the connector is mismated. The apparatus is configurable into two or more modes. The connector includes one or more pins for designating a mode of operation for the apparatus where the mode of operation can be selected from a continuous transmit mode and an intermittent transmit mode. The interface can include three pins which are configurable to select the mode of operation for the apparatus. The apparatus can include means for detecting a short circuit condition across a pair of the three pins and setting a mode identifier for the apparatus based on which pair of pins is identified as being shorted. The shorted pair of pins can provide the power interlock.

The transmitter can be a coil of a transformer that is operable to induce data signals for the frames from the transmitter to a complementary coil in a local receiver located in close proximity to the patient. The transmitter identifier can be derived from a pseudo-random number produced by the apparatus. The transmitter identifier can be derived from data samples from one or more sensors.

The apparatus can include signal conditioning means coupled between the interface and the data processor that are operable to condition data signals received from the sensors prior to processing by the data processor.

An adhesive can be applied to the first surface of the patch such that the first surface is adjacent to and fixedly attached to the skin of the patient. The patch can include a second surface opposite the first surface and where the second surface is adjacent to and fixedly attached to the skin of the patient.

The data processor can include a controller for selectively processing a subset of the frames. The controller can be configured to only pass the subset of frames to the transmitter for transmission to the local receiver.

In another aspect, the invention provides an apparatus for monitoring physiological data generated by sensors disposed on or in a patient. The apparatus includes a portable communications module in proximity to the sensors. The portable communications module includes a receiver operable to receive radio frequency signals including data frames representative of the physiological data and a detector for deciphering frames of data received by the receiver and rejecting frames from other devices in close proximity to the apparatus. A controller is included that is operable to compare data values for signals generated by the sensors with predetermined alarm functions and generate frames of data for transmission to a central monitoring station if an alarm is triggered. A location sensor is included for determining the location of the portable communications module. A transmitter module operates to, upon the detection of the alarm: initiate a communication link between the portable communications monitor and the central monitoring station, transmit physiological and location data and open a voice communication link between the central monitoring station and the patient.

Aspects of the invention can include one or more of the following features. The receiver can be one coil of a transformer where data signals are induced on the one coil from an associated coil in close proximity to the sensors. The location sensor can be a global positioning receiver. The transmitter module can include a cellular telephone.

In another aspect, the invention provides a patient monitoring system for monitoring physiological signals generated by sensors disposed on or in a patient. The patient monitoring system includes a patch and a portable communications module. The patch includes an interface, a data processor, transmitter and adhesive patch. The interface couples signals generated by the sensors to the data processor. The data processor operates to format data signals received into one or more frames of data where each frame includes a unique transmitter identifier. The transmitter operates to receive the frames from the data processor and broadcast the frames using radio frequency signals. The adhesive patch is adhesively attached to the patient and has a first surface on which the interface, data processor and transmitter are disposed.

The portable communications module is in proximity to the patch and includes a detector for deciphering frames of data received from a patch, a screening engine for screening communications transmitted by other patches and a controller. The controller operates to compare data values for signals generated by the sensors with predetermined alarm functions and generates frames of data for transmission to a central monitoring station if an alarm is triggered. The portable communications module includes a location sensor for determining the location of the communications module. The communications module operates to, upon the detection of the alarm, initiate a communication link between the portable communications monitor and the central monitoring station, transmit physiological and location data and open a voice communication link between the central monitoring station and the patient.

Among the advantages of the invention are one or more of the following. An inexpensive and reliable portable physiological signal monitor is provided that includes a disposable patch and communications module. The disposable patch includes signal condition electronics and means for collecting a plurality of data signals from sensors disposed on/in a patient. The disposable patch collects and forwards the data signals to the communications module for screening. The disposable patch includes a low power transmitter for transmitting the data using radio frequency signals. The transmitter is uniquely synchronized to the communications module at initialization to avoid detection and subsequent transmission of rogue data, e.g., from another disposable patch not attached but in proximity to the patient.

The communications module includes circuitry for locking onto the transmissions from a particular patch and for setting and detecting over limit conditions for the data signals representative of physiological problems of the patient. The communications module includes a controller for screening the received data signals from the disposable patch and eliminating rogue or clearly erroneous data. The communications module can include a telephone modem (cellular telephone) including a speaker and transmit/receiver pair that is configurable to both transmit data representative of the physiological condition of a monitored patient as well as voice data to and from the communications module and a central monitoring station. A user can be contacted using the voice channel and instructed or otherwise queried as to the patient's current medical emergency (or lack therein).

The communications module can be reused and is uniquely synchronized to a matching disposable sensor at each new use. The device can be used in plural modes including a continuous transmit mode and an intermittent transmit mode. When in continuous transmit mode, all data from the portable sensor is screened, formatted and passed to the central receiving station. In the intermittent mode, data is only transmitted when a local limit has been exceeded. The limits for each physiological signal can be set uniquely for each patient. The limits are stored locally in the communications module and can be downloaded at initialization or remotely downloaded at a later time.

Other advantages and features will be apparent from the following description and claims.

BRIEF DESCRIPTION OF THE DRAWINGS

FIG. 4a shows an initialization process for a patch.

FIG. 4b shows an initialization process for a communications module.

DETAILED DESCRIPTION

Figure 1:
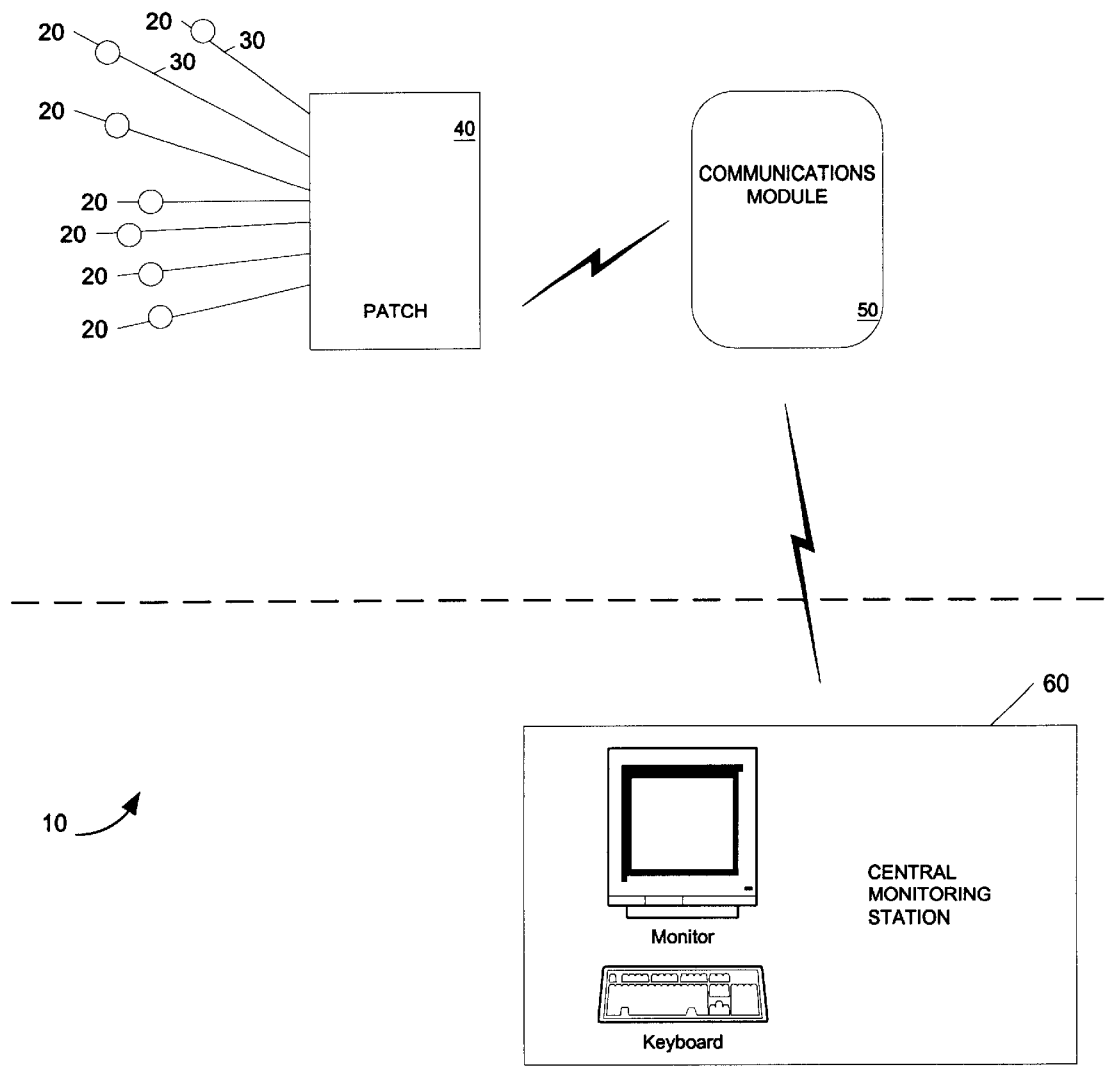
FIG. 1 is a schematic diagram of a physiological signal monitor system.

Referring to FIG. 1, a physiological signal monitor system 10 for remotely monitoring a patient includes a plurality of sensors 20, each coupled by leads 30 to a patch 40. System 10 includes a communications module 50 which receives signals from patch 40 and transmits data using radio frequency (RF) signals to a central monitoring station or terminal (CMS) 60.

Sensors 20 monitor the physiological condition of the wearer (patient). In one implementation the physiological data collected for the patient includes electrocardiogram (EKG) signals, temperature, respiration and blood pressure data. Other physiological data can be monitored including blood gas, respiration and the like. Each sensor can be coupled to patch 40 by one or more leads 30. For example, EKG sensor part number HP13943B, produced by the Hewlett Packard, Inc. of San Jose, Calif., can be used to monitor cardiac events and pulse data. The EKG sensor includes a series of sensor patches that are applied at various locations on the chest of the patient, each coupled by a single lead to patch 40. In one implementation, the sensor patches are inductive devices that are coupled to inductive port inputs on patch 40.

Temperature, blood pressure and respiration sensors can be resistive types that are coupled by one or more leads to resistive inputs on patch 40. A temperature sensor can be of the kind provided by Hewlett Packard, Inc. of San Jose Calif., part number HP21091A. A blood pressure sensor can be of the kind provided by SenSym, part number SCX08. The blood pressure sensor can provide both blood pressure and pulse data. A respiration sensor can be of the kind provided by Vernier Software, 8565 S. W. Beaverton-Hillsdale Highway, Portland, Oreg. 97225-2429, part number RMB. Various combinations of sensors can be coupled to patch 40, and as such, the particular combination disclosed herein should not be construed as limiting. In one implementation, only EKG and temperature sensors are coupled to patch 40.

Patch

Figure 2:
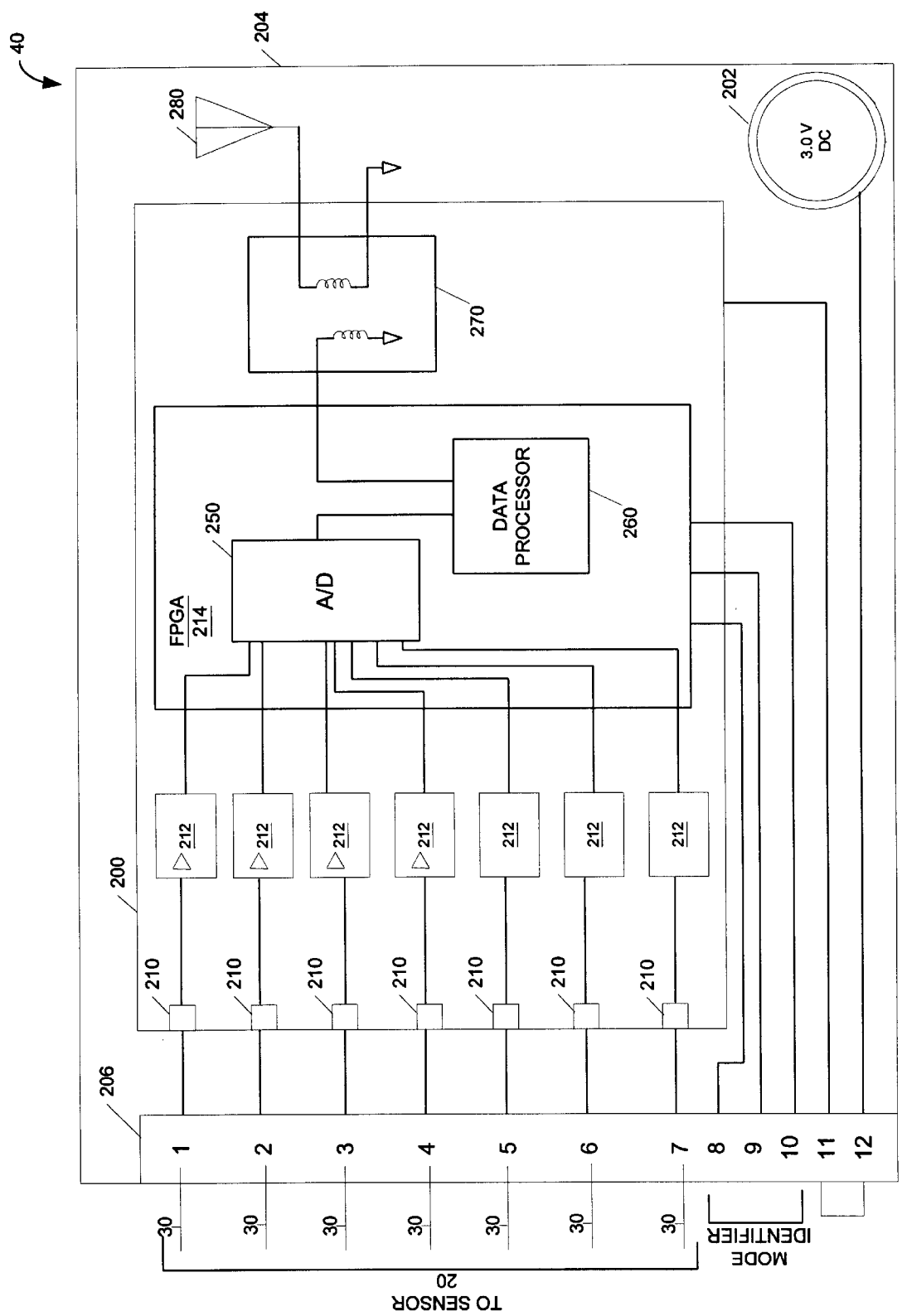
FIG. 2 is schematic diagram for a disposable patch.

Referring now to FIGS. 1 and 2, patch 40 includes a circuit board 200, a battery 202, adhesive patch 204 and interface 206.

Circuit board 200 includes a plurality of input ports 210, signal conditioning circuits 212, field programmable gate array (FPGA) 214, transmitter 270 and antenna 280.

Battery 202 provides power to signal conditioning circuits 212 and FPGA 214. In one implementation, the battery is a lithium type battery providing three (3.0) volts and approximately 1.5 ma of output current, part number U3V-LT, available from Ultralife Batteries, Inc.

Each input port 210 couples a lead from a sensor 20 through interface 206 to a signal conditioning circuit 212. The type of signal conditioning required depends on the nature of the input signal received. For inductive sensors, a step-up operational amplifier is coupled in-line between the respective input port 210 and the input of FPGA 214. The operational amplifier is a high impedance device that provides a high level of common mode rejection while amplifying the input signal prior to further processing by FPGA 214.

For resistive sensors, signal conditioning circuit 212 can include three legs of a whetstone bridge and power source. Signal conditioning for resistive sensors is well known in the art and as such, the details of such are omitted here for clarity purposes.

In one implementation, seven input ports 210 are included for monitoring EKG signals (4 leads), blood pressure, pulse and temperature of the patient.

FPGA 214 includes an analog to digital (A/D) convertor 250 and a data processor 260.

A/D convertor 250 decrypts the analog signals provided by the various sensors producing a digital output. The decryption is a transformation from analog to digital and can include signal level changes, DC offsets and the like. AID convertor 250 is configurable to sample the input signals at various sampling rates. In one implementation, A/D convertor 250 samples each channel at 800 samples per second. A/D convertor 250 includes a plurality of input channels for receiving input data (physiological signal data) and one or more output channels. A/D convertor 250 can be configured with a single output channel that provides a serial stream of data to data processor 260 or alternatively, can include a plurality of output channels, one corresponding to each input channel. In one implementation, A/D convertor 250 includes seven (7) input and seven (7) output channels for processing data from seven sensors. The output from each channel of A/D convertor 250 is coupled to data processor 260 for further processing.

Data processor 260 orders and packetizes the samples provided from A/D convertor 250 to produce frames of data. Each frame includes a header including a frame synchronization (sync) portion, a transmitter identifier (ID), mode identifier (mode ID), a correction code (CRC) and data samples collected from the various sensors. The frame sync portion includes a predefined pattern of bits that can be recognized by communications module 50 as a start of a new frame. Once frame synchronization is achieved, communications module 50 can lock onto the output signal provided from transmitter 270.

In one implementation, data processor 260 is programmable to configure the output frame according to the sensor types and data collection needs for each channel of data. One or more of the sensor data signals may need to be reported at high data rates to provide accurate measurements. Conversely, other sensor data signals may be associated with data that changes less frequently, and as such can be reported less frequently. Data processor 260 can decimate the data received from A/D convertor 250 to down sample each channel to an appropriate sample rate depending on the data signal type. In one implementation, five of the channels are sampled at approximately eight hundred (800) samples per second and are used to monitor high rate data, such as cardiac data collected by the EKG and blood pressure sensors. Other low rate data can be sampled at lesser sample rates, such as one hundred and ninety-four (194) samples per second for example, temperature data.

The transmitter ID is a unique identifier for a particular patch. In one implementation, the transmitter ID can be hard coded, wired, burned or otherwise set for a given patch. Alternatively, the transmitter ID can be adjusted using switches and the like. In one implementation, the transmitter ID is generated from data received at the patch. The linking of the transmitter ID and particular data signals can help in the differentiation of real data from rogue data at the communications module. In another implementation, the transmitter ID is generated using a pseudo-random number. More specifically, a data sample is selected, and depending on the value (i.e., the last digit of the data sample determines the amount of time to accumulate data), other data samples for one or more channels are accumulated. The accumulated data can be used to derive a transmitter ID. In one implementation, data is accumulated over all channels and a 16 bit transmitter ID is produced by applying a predefined function (hash) to the resultant data.

The mode ID can be set based on external pin connections detected on interface 206. The various modes of operation are described in greater detail below. In one implementation, the mode ID is combined with battery status information in an eight bit portion of the frame.

In one implementation, the frame produce by FPGA 214 is sized to be 720 bits in length and includes 672 bits of data samples eight (8) bits of header data, a sixteen (16) bit CRC, eight (8) bit mode data and a sixteen (16) bit transmitter ID. Data processor 260 outputs frames to transmitter 270 for forwarding to communications module 50. In one implementation, data processor outputs 8 k bits per second to transmitter 270 for forwarding to communications module 50.

Transmitter 270 and antenna 280 transmit frames of data from patch 40 to communications module 50. In one implementation, transmitter 270 and antenna 280 are combined in a single unit and can be of the form of a transformer. In one implementation, a ferrite core transformer is coupled between data processor 260 and a receiver in communications module 50. The receiver portion is described in greater detail below. Data signals are induced across the transformer coil in patch 40 and coupled to a corresponding coil in the receiver at communications module 50. In one implementation, a transformer is selected that produces a 175 kHz output signal that can provide 8 k bits of data throughput to communications module 50. In one implementation, the transmitter 270/antenna 280 combination includes a coil sized with approximately one hundred (100) turns 1"×2" effectively resulting in approximately a 1 mH inductive coil that has been custom wound or otherwise fabricated.

Patch 40 and communications module 50 can be collocated or in close proximity to each other on the patient's body. Alternatively, patch and communications module 50 can be separated, but the acceptable separation distance should be limited so as to keep the size, power consumption and cost of patch 40 to a minimum. In one implementation, transmitter 270 and antenna 280 are selected to provide a limited range, such as 10 feet. In one implementation, the antenna and transmitter pair is configured to broadcast over a range of only four (4) feet necessitating the wearing of communications module 50 on the body of the patient at all times.

Interface 206 includes a connector for receiving leads 30 from each of sensors 20, a power interlock and a mode identifier. In one implementation, a ten pin female connector is provided at interface 206 which can be mated to a cable bundle that includes leads 30. The cable bundle can include jumper wires for designating one of a preselected number of operational modes for the patch. In one implementation, three (3) pins are used to designate the operational mode for the system. The various modes of system 10 are described in greater detail below. A power interlock can be created using two pins of the interface connector. Power for the patch is coupled across the two pins. If an improper connection is made at the interface, the power interlock can cause the patch to be non-operational. Only if the power interlock is satisfied, for example by providing a short between the appropriate two pins in the interface using a jumper wire, will the patch function. In one implementation, the power interlock and mode selection are combined using three (3) pins. A jumper is placed across a pair of the three pins to provide the power interlock function. Depending on the combination of pins selected, a particular mode of operation is selected.

Patch 40 can be attached to the body of the patient using adhesive patch 204 and a conventional adhesive. Alternatively, other means can be used to attach patch 40 to the patient.

Communications Module

Figure 3:
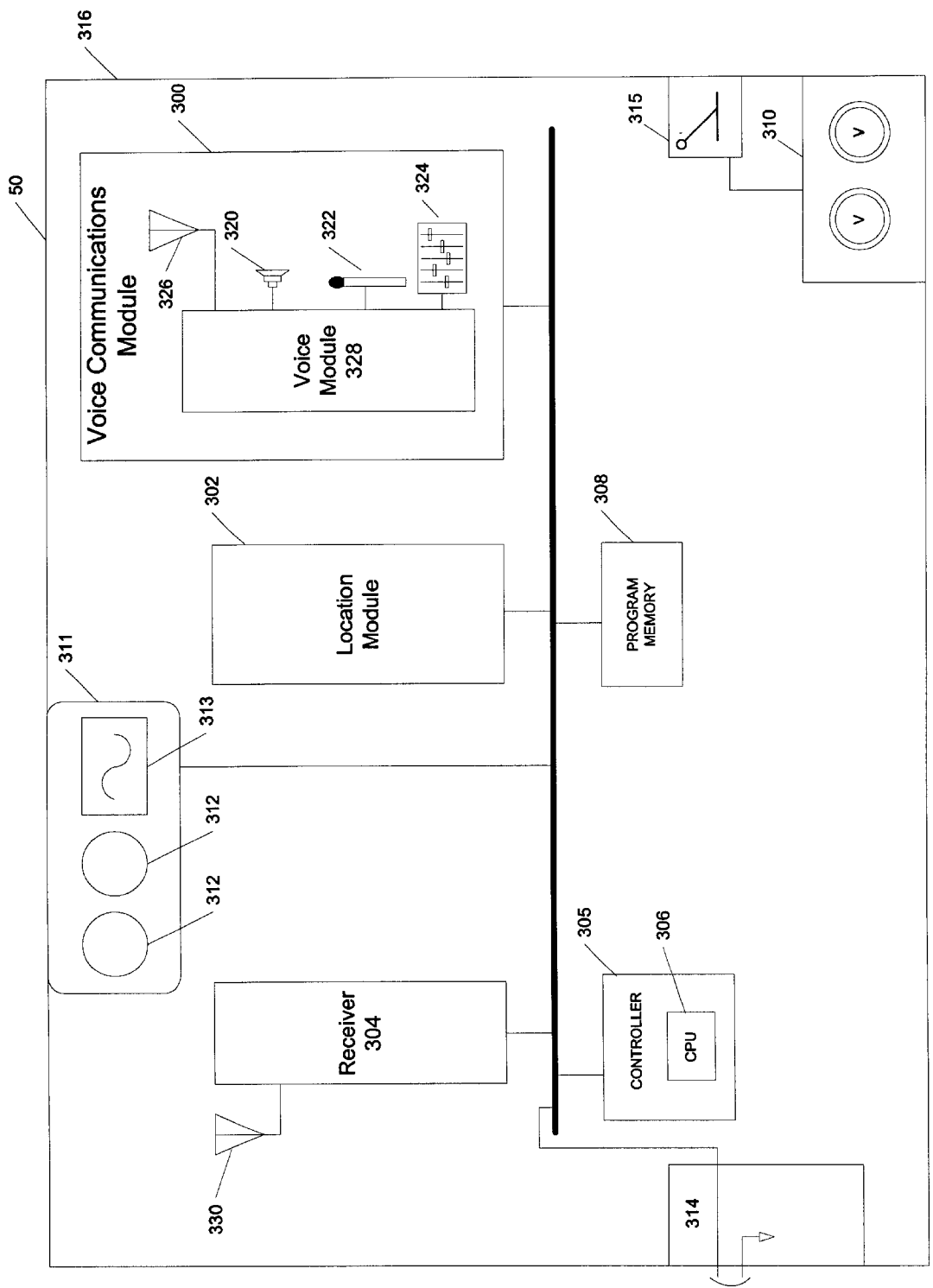
FIG. 3 is a schematic diagram for a communications module.

Referring now to FIGS. 1 and 3, communications module 50 interfaces between patch 40 and central monitoring station 60 and provides a user interface to the patient. The user interface includes a two-way voice communication channel, a data channel, a panic button, a visual indicator and an alarm. The user interface is described in greater detail below. Communications module 50 includes a voice communication module 300, a location module 302, a receiver 304, a controller 305 including a central processor 306, program memory 308, battery module 310, patient stimuli 311, panic button 314 and on/off switch 315, all of which are disposed within or on a housing 316.

Voice communications module 300 provides a data and voice communications channel between the patient and central monitoring station 60. When an alarm condition is triggered (as described in greater detail below), a voice channel is opened between the patient and the central monitoring station. Initially, the voice connection is used to transmit physiological and location data for the patient to the central monitoring station. After data has been received, an operator at the central monitoring station can use the open voice channel to communicate directly with the patient. The operation of the voice communication module is described in greater detail below. Voice communication module 300 includes a speaker 320, microphone 322, volume control 324, antenna 326 and voice module 328.

Speaker 320 is coupled to voice module 328 and broadcasts audible voice signals received from the central monitoring station to the patient. Microphone 322 is also coupled to voice module 328 and is operable to receive voice signals generated by a patient (or a patient's surroundings) and translate the received voice signals into analog or digital signals that can be conveyed to central monitoring station 60.

Volume control 324 can be a circuit that includes an electromechanical control (manual control knob) for adjusting the volume of the voice signals that are broadcast from speaker 320. Alternatively, the volume control circuitry can be contained within voice module 328 and only an electromechanical control may be included.

Antenna 326 receives/transmits analog or digital signals between voice module 328 and CMS 60 that include voice and data signals. Antenna 326 can be an omni-directional antenna and may be integral with voice module 328.

Voice module 328 can be a cellular telephone providing analog or digital signals representative of voice or data signals transferred between voice module 328 and central monitoring station 60. Voice module 328 can be of the form of a single mode analog phone or dual mode cellular telephone. Voice module 328 can be triggered by CPU 306 to initiate communications with central monitoring station 60. Alternatively, central monitoring station 60 can initiate a call to voice module 328 which is received by antenna 326 and forwarded to voice module 328. Data signals (data and voice) can be transmitted by central monitoring station 60, received by receiver 304, translated by voice module 328 and interpreted by CPU 306 to command or reprogram communications module 50. The downloading of data and commands are described in greater detail below.

Location module 302 provides information for locating the patient. Location module 302 can be of the form of a global positioning system (GPS) receiver that can use coarse or fine location algorithms to roughly or precisely locate a patient. The location data is transmitted along with any physiological data (alarm data) to central monitoring station 60. In one implementation, location module 302 detects a location at regular intervals, e.g., every five minutes, and stores the data (the last known position data) locally for faster recall. An alarm condition can trigger a location detection cycle, or alternatively, only the last known position data may be retrieved when transferring data to the CMS. In another implementation, the location of communications module 50 can be performed using network assisted cellular triangulation techniques, such as those used to locate 911 callers in a conventional cellular communications system.

Receiver 304 includes receive antenna 330 and is operable to receive data communications from patch 40. Data communications are received by receiver 304, screened by controller 305 and coupled to voice module 328 for broadcast to CMS through antenna 326. Receive antenna 330 can be of the form of an omni-directional antenna and can be integral with antenna 326. Alternatively, receive antenna 330 can be a directional antenna that is directed to specifically detect signals from a location at which patch 40 is mounted.

Controller 305 screens received physiological data (received from receiver 304), checks alarms, and constructs and forwards frames of data including physiological and location data to CMS 60. CPU 306 executes program instructions stored in program memory 308 to control the operation of communications module 50. The program instructions can be implemented in hardware, software or firmware and may be stored all or in part in program memory 308. If the program instructions are located in embedded firmware, no program memory may be required (other than conventional scratch memory). Alternatively, the central processing function can be implemented by a special purpose processor, digital signal processor or other means as is known in the art. The operation of communications module 50, as implemented when executing the program instructions, is discussed in greater detail below. Flow diagrams 4–8 describe the program steps executed by CPU 306 as embodied in the program instructions stored in program memory 308. The program instructions include instructions for: (1) detecting the mode of operation for the system; (2) monitoring received communications from patch 40 to detect alarm conditions in each data channel; (3) initiating communications with central monitoring station 60; (4) triggering location module 302 to detect a location of the patient; (5) packing alarm and location data into formatted frames for transfer to central monitoring station 60; (6) detecting and responding to panic alarms including opening a communication link to central monitoring station 60; and, (7) broadcasting received communications from central monitoring station 60. Other operations executed by CPU 306 include arrhythmia detection using algorithms stored in program memory 308.

Battery module 310 provides power to each of voice communications module 300, location module 302, receiver 304, controller 305 and program memory 308. In one implementation, battery module 310 provides 3.0 volts output at a nominal current, and includes a plurality of rechargeable lithium cells.

Patient stimuli 311 can include a visual indicator 312 and a vibrating means 313. Visual indicator 312 can include one or more light emitting diodes (LED) or other visual display. Visual indicator 312 can be used to indicate the operation of communications module 50 (i.e., the voice channel is open) or the communication link with patch 40. Vibrating means 313 can cause communications module 50 to vibrate indicating an alarm or receipt of a call from CMS 60.

Panic button 314 can be of the form of a switch or button that provides an interrupt to controller 305 to trigger a communication with CMS 60.

On/Off Switch 315 is coupled to battery 310 and controls the distribution of power throughout communications module 50.

Housing 316 can be of the form of a pager housing for enclosing the various communication module components in a conveniently sized package. The housing can include a belt attachment for allowing the communications module to be easily worn by a patient.

Central Monitoring Station (CMS)

CMS 60 includes a patient directory, a plurality of phone lines and one or more computing stations for tracking communications from various registered patients. Each computing station includes a user interface for displaying information relating to each registered patient. Registered patient refers to a patient that is currently communicating with CMS 60, either at the bequest of CMS 60 or the patient. The user interface can display patient data, a mode identifier and monitored data (retrieved from the communications module). The CMS monitors calls received, detecting panic requests, alarm requests, and data downloads. Panic requests can be given highest priority. Alarm requests can also be of high priority and each includes alarm data corresponding to the physiological data that is over limits for the patient. Data downloads can have the lowest priority, and are triggered when receiving calls from users operating in data acquisition mode where data is continuously (or near continuously) being received. CMS initiates telephone calls to patients, ambulances, doctors, police and other care providers depending on the nature of the data or requests received.

Operation

I. Initialization

At a time for initialization, an initialization process is performed including numerous individual steps by the various components of system 10. More particularly, each of patch 10 and communications module 50 have batteries installed or are otherwise activated. After activation, each unit (patch 40 and communications module 50) initiates an initialization procedure. Referring now to FIGS. 1 and 4a, the patch initialization procedure includes detecting a mode identifier based on the configuration of various pins of interface 206 (402). Once detected, the mode data is packed into a frame along with a transmitter ID and transmitted to communications module 50 (404). The physiological data can thereafter be processed including data sampling, decrypting and packetizing operations (406).

Referring now to FIG. 4b, at power up, a process 400 initiated by communications module 50 includes receiving data frames (410). Once lock is achieved (after the recognition of a sufficient number of consecutive data frames) (412), the transmitter ID for the particular patch included in the received frames is recorded (414). Thereafter, the transmitter ID is used to ensure that only data frames generating from a designated patch are processed by the particular communications module. In one implementation, the patch and data module are powered up side-by-side and are sufficiently isolated to ensure the two units synchronize to each other.

II. Alarm Mode

Figure 5:
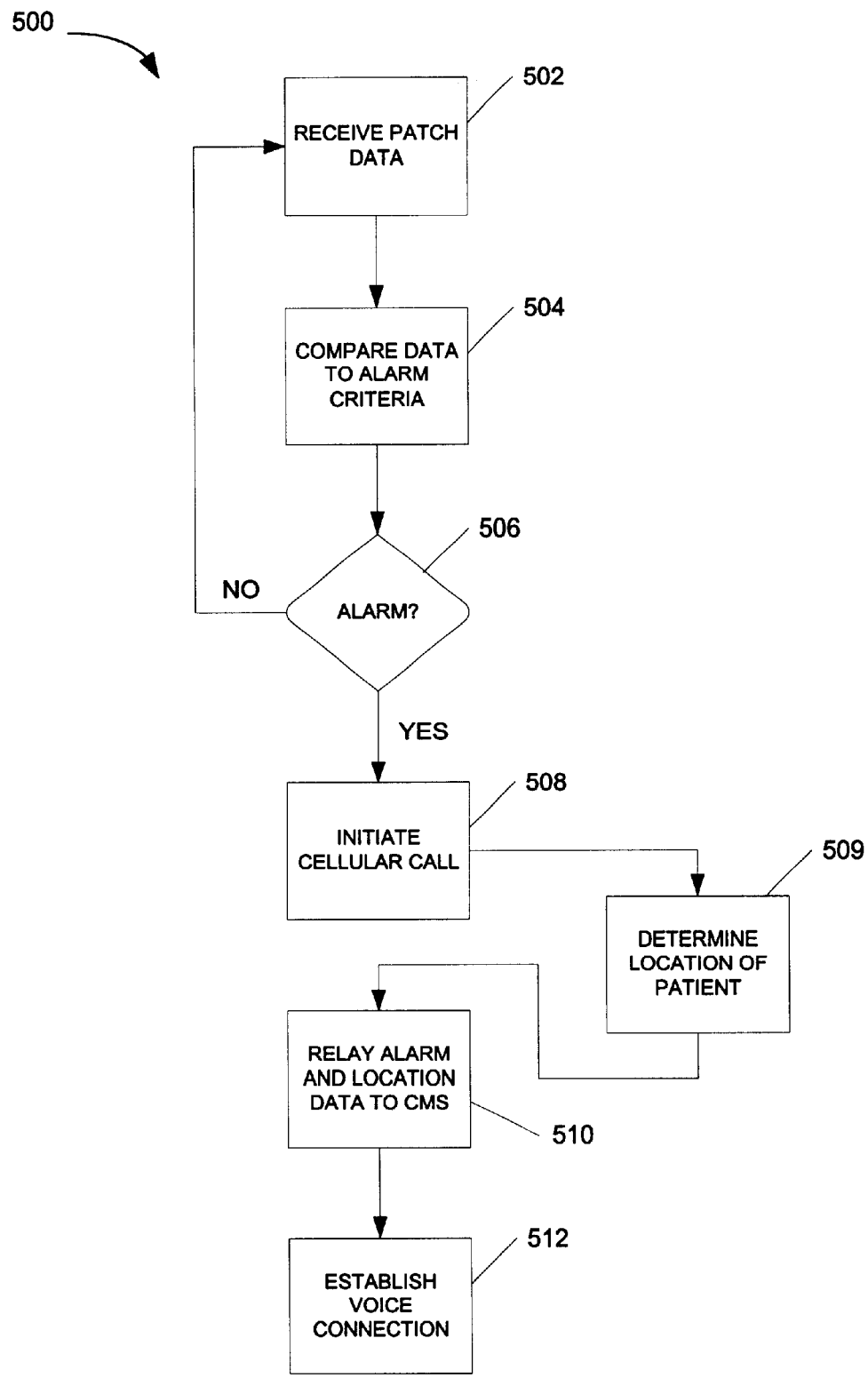
FIG. 5 shows a process for monitoring a physiological signal in accordance with the present invention when in alarm mode.

The default mode for communications module 50 is the alarm mode. When configured in alarm mode, data signals from a patient's patch are continuously monitored against a set of predefined alarm limits. When an alarm condition is detected, a communications channel is opened to central monitoring station 60 and data and voice communications can be initiated. Referring now to FIGS. 1 and 5, a flow diagram for an alarm mode process 500 as executed by communications module 50 is shown. Communications module 50 receives data from patch 40 continuously (502). In one implementation, seven channels of data (each sampled at various rates) are evaluated against alarm criterion (504). Each data channel has an associated trigger function that is evaluated. The trigger function can include both a threshold value as well as a duration time. If the threshold value is exceeded for the designated duration time, then an alarm is set.

If an alarm is detected (506), a cellular phone call is initiated, using voice communications module 300, to CMS 60 (508). The location of the patient is determined (509). Once the phone call is connected, alarm data (including patient location data) is relayed to CMS 60 (510). The alarm data can include data from all channels or can be limited to only the particular alarm channel data. In one implementation, the data received from patch 40 is down sampled and then provided to CMS 60. More specifically, CPU 306, executing program instructions stored within communications module 50, formats data packets for transfer to CMS 60. As described above, the data packets include the alarm data and location data.

Thereafter a voice connection with the patient is established (512). Depending on the nature of the alarm, and the reasons therefore, the patient may be instructed by an operator at CMS 60 to take a medication, check the operation of a unit, verify a location or other action, as appropriate.

III. Data Acquisition Mode

Figure 6:
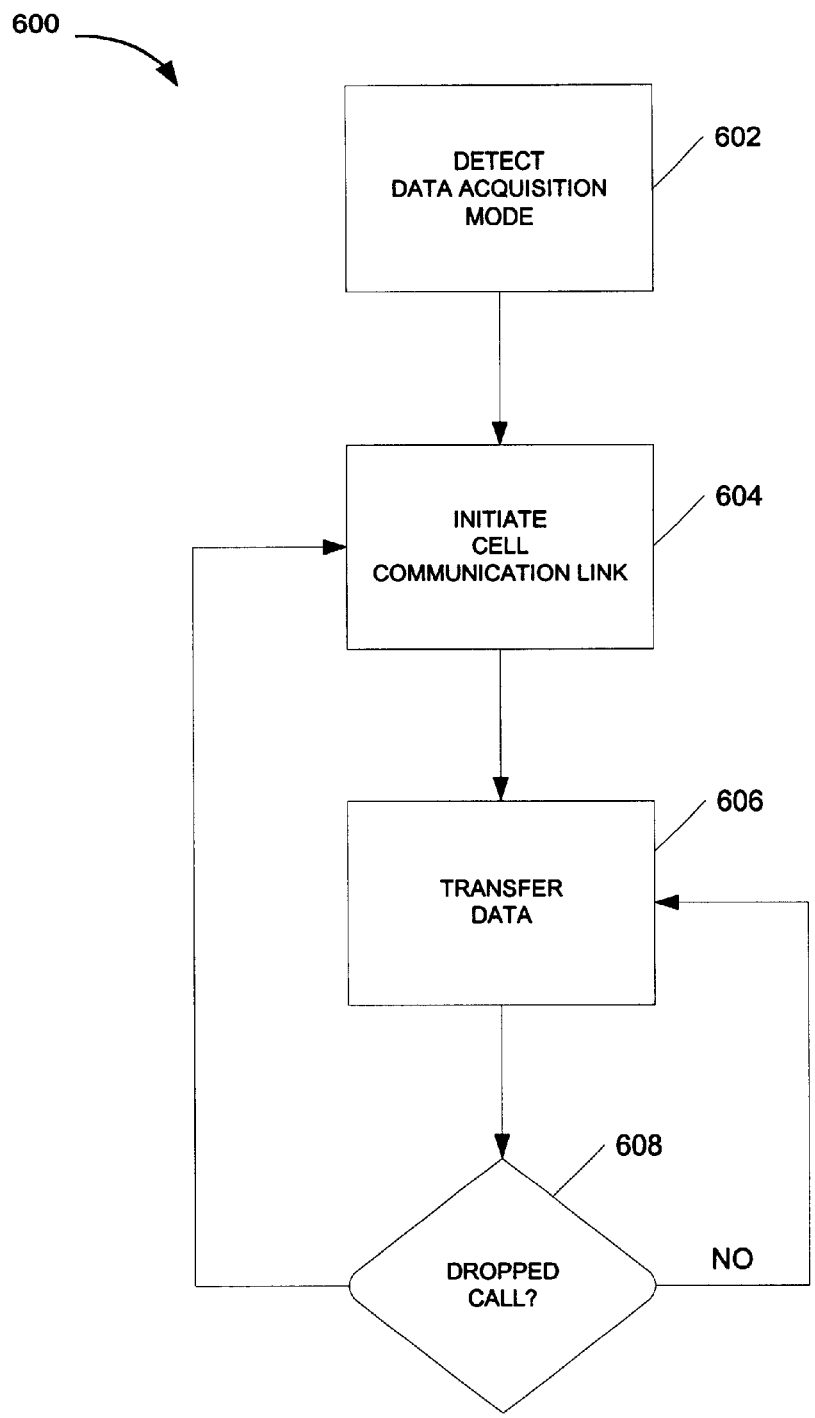
FIG. 6 shows a process for monitoring a physiological signal in accordance with the present invention when in data acquisition mode.

Just as in the alarm mode, the patient wears a patch connected to various sensors. Patch 40 continuously transmits data to communications module 50. Referring now to FIG. 6, a data acquisition process 600 begins by detecting the data acquisition mode designation at initialization (602). Thereafter, communications module 50 initiates and maintains a cellular communication link with CMS 60 (604) and continuously transfers data for all channels (606) via the cellular communication link (608). Communications module 50 can provide an indication to the patient (an LED) if patch 40 to communications module 50 transmissions are disrupted, or if the cellular phone call is interrupted.

III. Panic Mode

Figure 7:
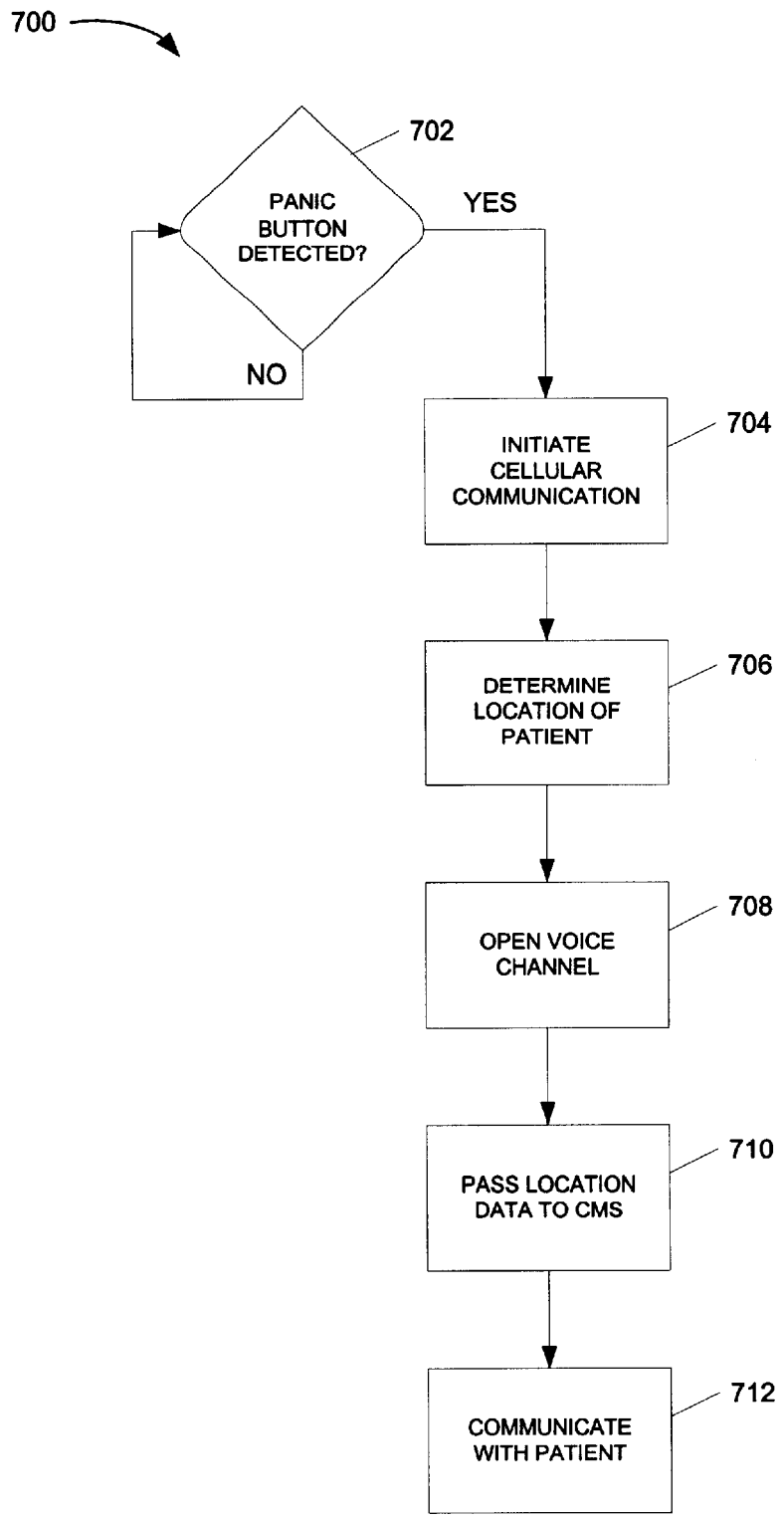
FIG. 7 shows a process for monitoring a physiological signal in accordance with the present invention when in panic mode.

If the patient needs immediate assistance (e.g. "I've fallen and can't get up."), he/she can press panic button 314 which causes the communications module to initiate a panic process 700 as shown in FIG. 7. More specifically, communications module 50 detects the depressing of panic button 314 (702) and initiates a cellular communication (704). Controller 305 initiates a location event that triggers the location module to determine the location of the patient (706). A voice channel is opened between the patient and CMS 60 (708) and the location data is passed directly to CMS 60 (710). Thereafter, the voice channel can be used by both the operator at CMS 60 and the patient to evaluate the nature of the emergency (712). The voice channel can be used to alternate between voice communications and data transfers from the communications module depending on the direction provide from CMS 60.

IV. Check-on Patient Mode

Figure 8:
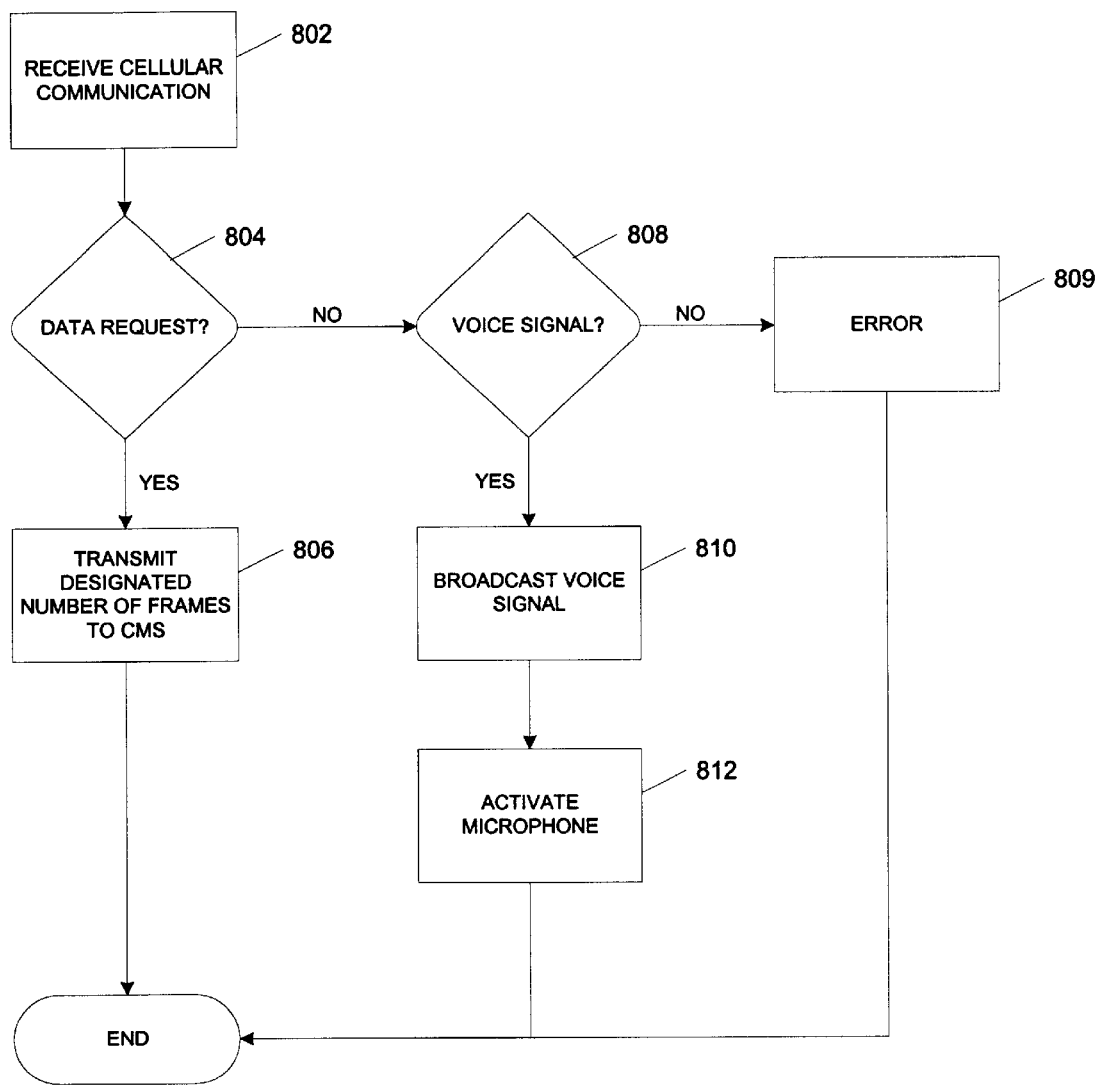
FIG. 8 shows a process for monitoring a physiological signal in accordance with the present invention when in check mode.

The check-on patient mode can be used to retrieve physiological data or feed-back from the patient directly. Referring now to FIG. 8, the check-on patient mode is triggered by the receipt of a cellular communication by receiver 304 (802). If a data request is detected (804), a designated number of frames of data can be transmitted back to CMS 60 (806). If a voice signal is detected (808), then the voice signal can be broadcast on speaker 320 (810) and microphone 322 can be activated to receive voice signals from the patient (or the patient's surrounding) (812). Else, an error is registered and the call is terminated (809). The voice channel is maintained until the cellular connection is dropped or otherwise terminated by CMS 60.

V. Programming Mode

CMS 60 or other "host" can configure the communications module's programmable parameters using a cellular phone link. In one implementation, a programming mode is entered upon receipt of a cellular call by receiver 304 and the detection of a programming command. Programming commands can be used to download new trigger data, new sample rates, or new program instructions for operating communications module 50. If a programming command is detected, a designated number of bytes are downloaded from CMS 60 or other host.

Alternative Implementations

In one implementation, communications module 50 includes no on board memory for storing or otherwise accumulating data collected from patch 40. Alternatively, the module can be configured to include a memory sufficiently sized so as to maintain a predefined amount of data prior to download, for example at a future time.

The voice communications module can be a pager that provides visual messages to the patient. The housing can be configured with one or more buttons or a keypad to allow for rudimentary communications between the central communications station and the communications module.

In one implementation, the data acquisition mode is modified to provide monitoring at less than a continuous duty cycle. More specifically, in one implementation, the data transmitted from the patch is cycled, toggling on and off, while providing data to the communications module. When in the modified mode, battery power can be preserved while still allowing for the near continuous monitoring of a patient. In one implementation, a ⅙ duty cycle is used, where patch 40 transmits to communications module 50 only one out of every six frames produced.

In one implementation, data received from patch 40 can be compressed prior to inclusion in data frames transmitted by the communications module to CMS 60. The compression can be of the form of an entropy encoding for minimizing a number of bits required to represent a data frame or fractal compression can be used.

In one implementation, controller 305 includes an interface for directly transferring data to CMS 60 without using the cellular communications link. In one implement, an RS-232 serial port is provided to allow for the download of data to another device (modem, computer or the like) to allow for an alternate means of communicating in the event the cellular connection is down or otherwise unavailable.

The present invention has been described in terms of specific embodiments, which are illustrative of the invention and not to be construed as limiting. Other embodiments are within the scope of the following claims.

What is claimed is:

1. An apparatus for monitoring physiological data generated by a plurality of sensors disposed on or in a patient, the apparatus comprising:

an interface operable to receive data signals generated by the plurality of sensors;

a data processor coupled to the interface and operable to format data signals received from the interface into one or more frames of data, the data processor operable to generate a transmitter identifier based on sensor data received from one or more of the plurality of sensors, the data processor operable to format frames where each frame includes the transmitter identifier that is unique to the apparatus;

a transmitter operable to receive the frames from the data processor and broadcast the frames using radio frequency signals to a local receiver located in close proximity to the patient; and a patch adapted to be attached to the patient and having a first surface on which the interface, data processor and transmitter are disposed.

2. The apparatus of claim 1, wherein the patch is attached using an adhesive.

3. The apparatus of claim 1, wherein the interface includes a connector and a power interlock, the connector coupling lead wires from the sensors to the apparatus and the power interlock operable to disable the apparatus when the connector is mismated.

4. The apparatus of claim 3, wherein the apparatus is configurable into two or more modes, and where the connector includes one or more pins for designating a mode of operation for the apparatus where the mode of operation is selected from a continuous transmit mode and an intermittent transmit mode.

5. The apparatus of claim 4, wherein the interface includes three pins configurable to select the mode of operation for the apparatus, where the apparatus includes means for detecting a short circuit condition across a pair of the three pins and setting a mode identifier for the apparatus based on which pair of pins is identified as being shorted, and where the shorted pair provides the power interlock.

6. The apparatus of claim 1, wherein the transmitter is a coil of a transformer that is operable to induce data signals for the frames from the transmitter to a complementary coil in the local receiver located in close proximity to the patient.

7. The apparatus of claim 1, wherein the transmitter identifier is derived from a pseudo-random number produced by the apparatus.

8. The apparatus of claim 7, wherein the transmitter identifier is derived from data samples from one or more sensors.

9. The apparatus of claim 1, further comprising:
signal conditioning means coupled between the interface and the data processor and operable to condition data signals received from the sensors prior to processing by the data processor.

10. The apparatus of claim 1, wherein an adhesive is applied to the first surface of the patch such that the first surface is adjacent to and fixedly attached to the skin of the patient.

11. The apparatus of claim 1, wherein the patch includes a second surface opposite the first surface and where the second surface is adapted to be adjacent to and fixedly attached to the skin of the patient.

12. The apparatus of claim 1, wherein the data processor includes a controller for selectively processing a subset of the frames and configured to only pass the subset of frames to the transmitter for transmission to the local receiver.

13. An apparatus for monitoring physiological data generated by sensors disposed on or in a patient, the sensor data aggregated and transmitted as frames of data from a transmitting device located on or in the patient, the apparatus comprising:
a portable communications module in proximity to the sensors and including
a receiver operable to receive radio frequency signals including data frames representative of the physiological data, the data frames including a unique transmitter identifier for identifying a particular transmitting device;
a detector for deciphering frames of data received by the receiver and rejecting frames from other devices in close proximity to the apparatus, the detector including a screening engine for initializing communications with the transmitting device and operable to process frames received during an initialization period including store the unique transmitter identifier associated with the transmitting device, the screening engine operable after the initialization period to compare a transmitter identifier received with each frame with the stored unique transmitter identifier and reject received frames whose transmitter identifier does not match the stored unique transmitter identifier,
a controller operable to compare data values for signals generated by the sensors with predetermined alarm functions and generate frames of data for transmission to a central monitoring station if an alarm is triggered,
a location sensor for determining the location of the portable communications module, and
a transmitter module operable to, upon the detection of the alarm, initiate a communication link between the portable communications module and the central monitoring station, transmit physiological and location data and open a voice communication link between the central monitoring station and the patient.

14. The apparatus of claim 13, wherein the receiver is one coil of a transformer, and where data signals are induced on the one coil from an associated coil in close proximity to the sensors.

15. The apparatus of claim 13, wherein the location sensor is a global positioning receiver.

16. The apparatus of claim 13, wherein the transmitter module includes a cellular telephone.

17. A patient monitoring system for monitoring physiological signals generated by a plurality of sensors disposed on or in a patient, the patient monitoring system comprising:
a patch including an interface, a data processor, a transmitter and an adhesive patch,
the interface coupling signals generated by the plurality of sensors to the data processor,
the data processor operable to
format data signals received into one or more frames of data,
generate a unique transmitter identifier based on sensor data received from one or more of the plurality of sensors including generating a pseudorandom number, accumulating data for a time period whose length is based on the pseudorandom number and deriving the unique transmitter identifier from the accumulated data, and
format frames where each frame includes the unique transmitter identifier,
the transmitter operable to receive the frames from the data processor and broadcast the frames using radio frequency signals, and
where the adhesive patch is adapted to be adhesively attached to the patient and having a first surface on which the interface, data processor and transmitter are disposed;
a portable communications module in proximity to the patch, the portable communications module including
a detector for deciphering frames of data received from a patch,
a screening engine for screening communications transmitted by other patches, the screening engine operable to initialize communications with the transmitter and to process frames received during an initialization period including store the unique transmitter identifier associated with the transmitter, the screening engine operable after the initialization period to compare a transmitter identifier received with each frame with the stored unique transmitter identifier and reject received frames whose transmitter identifier does not match the stored unique transmitter identifier,
a controller operable to compare data values for signals generated by the sensors with predetermined alarm functions and generate frames of data for transmission to a central monitoring station if an alarm is triggered,
a location sensor for determining the location of the communications module, and
a communications module operable to, upon the detection of the alarm, initiate a communication link between the portable communications monitor and the central monitoring station, transmit physiological and location data and open a voice communication link between the central monitoring station and the patient.

18. The patient monitoring system of claim 17, wherein the patient monitoring system is configurable into two or more modes, and where the interface includes one or more pins for designating a mode of operation for the patient monitoring system where the mode of operation is selected from a continuous transmit mode and an intermittent transmit mode.

19. The patient monitoring system of claim 17, wherein the transmitter is a first coil of a transformer and where a second complementary coil of the transformer is included in the detector and where the transmitter is operable to induce data signals for the frames from the first coil to the complementary second coil in the portable communications module.

20. The patient monitoring system of claim 17, wherein the transmitter identifier is derived from a pseudo-random number produced by the patient monitoring system from data samples received at the patch.

21. The patient monitoring system of claim 17, wherein the first surface of the patch includes an adhesive such that the first surface is adapted to be adjacent to and fixedly attached to the skin of the patient.

22. The patient monitoring system of claim 17, wherein the patch includes a second surface opposite the first surface and where the second surface is adapted to be adjacent to and fixedly attached to the skin of the patient.

23. The patient monitoring system of claim 17, wherein the data processor includes a controller for selectively processing a subset of the frames and configured to only pass the subset of frames to the transmitter for transmission to the portable communications module.

* * * * *